United States Patent [19]

Clark et al.

[11] 4,098,291
[45] Jul. 4, 1978

[54] PRESSURE RELIEF VALVE

[75] Inventors: Thomas W. Clark, Clearwater; William E. Hale, Dunedin, both of Fla.

[73] Assignee: Manoscope, Inc., Clearwater, Fla.

[21] Appl. No.: 731,455

[22] Filed: Oct. 12, 1976

[51] Int. Cl.² ............................................. F16K 11/18
[52] U.S. Cl. .............................. 137/871; 137/625.68; 128/2.05 G
[58] Field of Search ...................... 137/625.68, 625.67, 137/612.1; 128/2.05 G

[56] References Cited

U.S. PATENT DOCUMENTS

| | | | |
|---|---|---|---|
| 527,381 | 10/1894 | VanTine | 137/625.68 |
| 2,591,118 | 4/1952 | Bent | 137/625.67 |
| 2,979,080 | 4/1961 | Hewitt | 137/625.68 |
| 3,254,671 | 6/1966 | Berliner | 128/2.05 G |
| 3,504,663 | 4/1970 | Edwards | 128/2.05 G |
| 3,823,707 | 7/1974 | Hayes | 128/2.05 G |

FOREIGN PATENT DOCUMENTS 577,613   7/1924   France .......................... 128/2.05 G

*Primary Examiner*—Arnold Rosenthal
*Attorney, Agent, or Firm*—Duckworth, Hobby, Allen & Pettis

[57] ABSTRACT

A pressure relief valve of the type primarily designed to regulate the flow of fluid generally in the form of air and its rate of flow and capability of being utilized in combination with a sphygmomano-meter assembly whereby flow of fluid from the sphyg head is accomplished at a predetermined rate and is selectively regulated by manual manipulation of the valve assembly. A valve housing is movably mounted therein and a valve block which is disposed to establish fluid communication from a sphyg head or point of use of the fluid through a metered port so as to establish a flow path for the fluid exiting from the valve assembly at a predetermined rate.

14 Claims, 2 Drawing Figures

PRESSURE RELIEF VALVE

BACKGROUND OF THE INVENTION

1. Field of the Invention

This invention relates to a pressure relief valve capable of regulating the flow of fluid from a point of use to atmosphere at a predetermined rate by the direction of the fluid flow path from its point of use through at least one metered aperture or port assembly.

2. Description of the Prior Art

In modern medical practice the monitoring of blood pressure is an extremely common and well established practice. More specifically, with relatively recent medical developments relating to the control of unnecessarily high blood pressure of a patient, there has been a movement to urge affected members of the population to obtain facilities for measuring their own blood pressure.

In application, a pressure cuff or sleeve is placed in substantially surrounding relation to the arm somewhat in spaced relation above the elbow. The pressure cuff is pressurized through the application of air, under pressure, to a bladder or like structure contained within the pressure cuff. Pressure is generally applied by means of a hand manipulated squeeze bulb structured with a one-way valve so as to direct air or like fluid under pressure from the bulb to the bladder of the pressure sleeve as set forth above. A sphygmomanometer head is interconnected in fluid communication to the cuff for the purpose of measuring the arterial and venous pressure of the patient. Both systolic and diastolic pressures are determined through listening through the stethoscope to the pulse, or otherwise monitoring, as the pressure is released in a regulated fashion from the cuff. This release of pressure conventionally is accomplished through a simplified release valve in the form of a threaded connector. In operation, rotation of the threaded connector to its open position serves to vent the pressurized fluid from the pressure cuff. The rate of fluid flow and pressure release is determined by the amount of removal of the threaded connector or valve element from the remaining valve assembly.

In the most popular prior art devices, such release cannot be controlled within specified limits thereby resulting in irregular rates of flow or release of pressure during the measurement of the blood pressure and the observance of the sphyg head.

The sphyg head presents visual indication of the respective systolic and diastolic pressures as indicated thereon by coordinating recognizable sounds or changes in the audio or other report of the pulse. In that audio or other method of detection of this pulse is dependent upon the rate of release of the pressure or air flow from the pressurized cuff, the operator of the sphygmomanometer observes operation of the sphyg head at different rates. This non-uniform performance of the sphyg head again, due to the erratic rate of fluid flow from the pressurized cuff, frequently results in multiple performances of the entire monitoring process in order to obtain an accurate, reliable measurement of arterial pressure.

Accordingly, it can be readily seen that it would be highly desirable to accomplish a standard rate of fluid flow of the pressurized air or fluid from the pressure cuff during the observance of the sphyg head. Greater accuracy and efficiency would result in standard rates of release of the pressure from the pressurized cuff.

Accordingly, there is a great need in the medical profession for a valve structure being of relatively simple design and capable of efficiently and effectively releasing fluid from the pressure cuff at an adjustable, consistent rate.

SUMMARY OF THE INVENTION

The present invention is directed towards a valve assembly of the type primarily designed but not limited to application in a sphygmomanometer assembly. More specifically, the valve assembly of the present invention is used to control direction and rate of fluid flow both to and from a pressure cuff of the type primarily used in the monitoring of blood pressure in a human patient. However, it should be noted that the valve structure of the present invention is adaptable for efficient and effective utilization in any particular application wherein it is required to direct and control the rate of fluid flow to and/or from a source to a point of use.

The valve structure of the present invention comprises a valve housing having a cylinder formed therein and conduit means comprising at least a first and second conduit element. The first conduit element, in the preferred embodiment, is disposed in fluid communication between a fluid source and the cylinder within the housing while the second conduit element is disposed between the cylinder within the housing and the point of use of the fluid exiting the housing under pressure which is originally derived from the fluid source itself. In the conventional application the fluid source may take the form of a squeeze, flexible bulb normally capable of being hand manipulated so as to direct fluid flow therefrom, primarily in a single direction due to the provision of a check valve disposed within the first conduit element.

A valve block is movably mounted within the cylinder means of the housing and positionable therein so as to regulate both direction and rate of fluid flow, as will be described in greater detail hereinafter.

The valve block means is disposed and configured for reciprocating movement substantially along its longitudinal axis within the cylinder means of the housing. A fluid flow path means is formed on the block and comprises at least a first and second fluid flow path disposed in spaced apart, at least partially segregated relation to one another, so as to regulate the direction or channeling of the fluid as it passes through the housing by means of either the first or second conduit element. More specifically, in the preferred embodiment, the first fluid flow path is integrally formed on the valve block and specifically disposed to be positionable so as to establish fluid communication between the first conduit element and the second conduit element so as to allow fluid to pass from the fluid source, through the valve block, to the second fluid conduit and eventually to the point of use of the pressurized fluid. As will be explained in greater detail hereinafter, a relief valve means is also disposed in fluid communication with said fluid flow path means and more particularly said first fluid flow path.

The second fluid flow path is formed on said valve block means in spaced relation to said first fluid flow path and disposable to establish fluid communication between the point of use of the pressurized fluid and a fluid exit assembly. In this particular disposition, fluid is prevented from exiting back into the fluid supply source due to the provision of the check valve disposed in fluid regulating position between the fluid supply source and the first conduit element. Seal means in the form of a plurality of sealing elements are disposed in fluid sealing engagement between the outer surface of the valve block and the inner surface of the cylinder formed within the housing. The provision of these sealing elements is such as to establish fluid segregation between the first conduit element and the second conduit element.

With regard to the relief valve means, a first fluid channel is integrally formed at least partially on the interior of the valve block means and disposed in direct fluid communication between the first fluid flow path and the relief valve means. Further structural features of the relief valve means comprise a relief port disposed to vent fluid from the valve block and more specifically, fluid issuing from the first fluid channel to the atmosphere on the exterior of the valve housing. A sealing means is disposable in adjustable, fluid sealing engagement between the first fluid channel and the relief port of the relief valve means. This sealing means is adjustable into and out of sealing engagement relative to the relief exit port by means of a hand or finger manipulated adjusting means which, in the preferred embodiment, takes the form of a push knob rotationally connected to the relief valve means and, by virtue of this rotational connection, movable into and out of positioning engagement with the sealing means and specifically in regard to the disposition of the sealing means relative to the relief port described above.

In addition to the first fluid channel, a second fluid channel is disposed to establish direct fluid communication between the second fluid flow path and the fluid exit assembly, briefly described above. The fluid exit assembly, by virtue of the disposition of the second fluid channel, is brought into direct fluid communication with the pressurized fluid or air returning from the point of use of the pressurized fluid for the purpose of being exited from the housing through the valve block means. An important feature of the present invention is the provision of the establishment of a consistent rate of release of this pressurized fluid for the purpose of monitoring the operation and visual indication of the sphygmomanometer head while the pressure is being reduced at a constant rate. Accordingly, the fluid exit assembly comprises an aperture means disposed in direct communication to the second fluid channel and being of a specific, predetermined dimension which will allow exiting of the pressurized fluid from the valve body at a constant rate, as set forth above.

Other structural features of the present invention include the provision of a bias means mounted on the valve housing and disposed in biasing relation to the valve block means so as to normally bias the valve block to establish fluid communication between the fluid supply source, the valve block means, and the point of use of the pressurized fluid. This specific disposition calls for the first fluid flow path to be disposed in communicating relation to both the first fluid conduit and the second fluid conduit to establish the direction of flow as immediately set forth above. In addition, this specific position of the valve body, in its normally biased position, allows the first fluid channel to be disposed in direct fluid engagement with any pressurized fluid returning through the second fluid conduit element to accomplish complete release or exiting of the pressurized fluid through the relief valve means after visual monitoring of the sphygmomanometer head has been accomplished.

Disposition of the valve block means so as to establish direct fluid communication between the conduit means and the second fluid flow path serves to further establish direct fluid communication with the fluid exit assembly thereby placing the valve block and accordingly the entire valve assembly in a position for release of the pressurized fluid from the pressure cuff, through the valve housing, at a consistent rate for the purpose as set forth above.

Other structural features of the present invention comprise the provision of stop elements mounted at substantially opposite ends of the cylinders so as to limit, within predetermined ranges, the reciprocal movement of the valve block means within the cylinder.

In operation, an operator of the valve assembly of the present invention allows the valve block means to move to its normally biased position such that the first fluid flow path is disposed in direct fluid communication between the conduit means such that fluid exiting from the fluid supply means through the check valve is transferred directly through the valve block means to the point of use of the pressurized fluid. As set forth above, automatic return of this pressurized air into the bulb comprising the fluid source is prevented through the provision of a one-way check valve disposed in fluid regulating position between the fluid supply source and the first conduit element. After the cuff and monitoring sphyg head have been pressurized to the desired point, the valve block means is merely movably adjusted, along its axis, within the cylinder by means of depression of the push knob integrally or otherwise attached thereto. This force is exerted thereon to a sufficient degree to move the valve block means against the biasing means. In this position, the second fluid flow path is disposed in direct fluid communication with the fluid conduit means so as to allow pressure to return from the pressurized cuff and the sphyg head through the second conduit element, into the valve block means, and to the fluid exit assembly through the second fluid channel. Regulated release of the pressurized fluid is accomplished through its exiting through the metered aperture or aperture having a predetermined direction which comprises part of the fluid exit assembly.

As set forth above, pressurized fluid exiting in this manner does so at a constant rate due to the predetermined dimension of the exiting aperture.

Upon completion of the visual and audio monitoring cycle, the remainder of the pressurized fluid is easily releasable by release of axial pressure on the push knob and the rotational movement of the knob itself so as to disengage the sealing means from the exit port formed as part of the relief valve means. This in turn establishes fluid communication between the exterior of the valve housing, through the exit port, as the pressurized fluid travels back from the pressure cuff through the second fluid conduit and through the first fluid channel.

The invention accordingly comprises the features of construction, combination of elements and arrangement of parts which will be exemplified in the construction hereinafter set forth, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
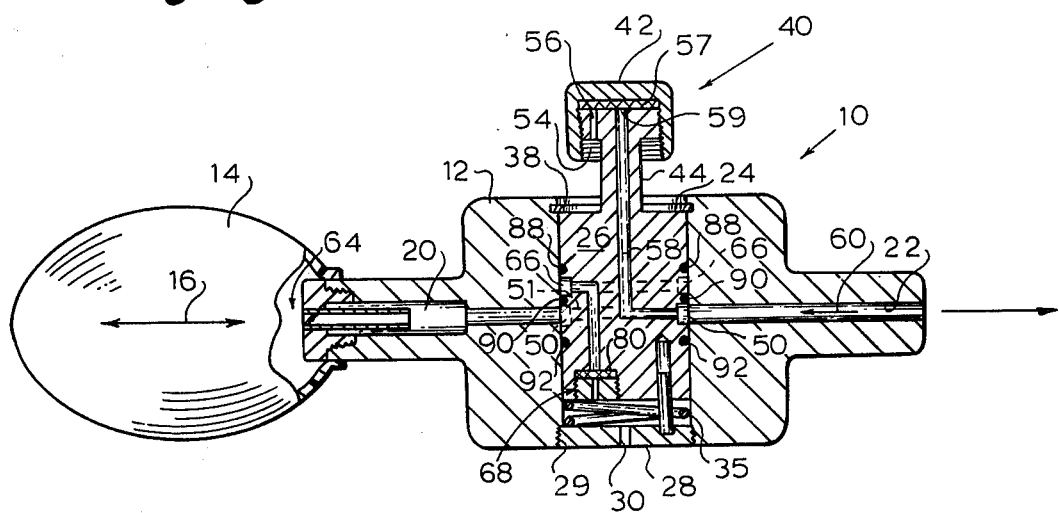
FIG. 1 is a sectional view showing the valve block disposed within the cylinder of the valve housing so as to establish direct fluid communication between the supply source and the point of use.

As shown in FIG. 1, the valve assembly of the present invention is generally indicated as 10 and comprises a valve housing 12 having a fluid supply source 14 attached thereto. In the preferred embodiment, the fluid supply source comprises a "squeeze bulb" of the type conventionally used in the medical profession for pressurizing pressure cuffs and like structures during the application of a sphygmomanometer in the taking of blood pressure from a human patient. Depression and release of the fluid supply source is generally indicated by directional arrows 16 and 18, respectively. More specifically, the contraction or depression, by hand, of the squeeze bulb causes fluid to flow through the conduit means of the valve housing which comprises a first conduit element 20 and a second conduit element 22. The conduit elements lead to and from a cylinder means 24 formed within the housing whereby fluid communication is established between the fluid supply source 14 directly disposed in fluid engagement with the first fluid conduit element 20 and the point of use of the pressurized fluid (not shown) which is disposed in direct fluid communication with the second fluid conduit element 22.

A valve block means 26 is disposed in movably mounted position on the interior of the cylinder and specifically configured to be reciprocally mounted therein in a direction substantially corresponding to the longitudinal axis of the valve block means 26. A closing disc 28 is screw threaded as at 29 or otherwise attached to the housing 12 so as to substantially close off the lower portion of the cylinder 24. A vent means 30 is formed in the closing disc 28 so as to release the pressurized fluid therefrom in a manner which will be described in greater detail hereinafter. The release of this pressurized fluid 32 is generally indicated by directional arrow 34 as shown in FIG. 2.

A biasing means in the form of spring elements 35 is disposed in biasing relation to the valve block means 26 so as to normally bias this valve block means into engagement with the stop element 38 which may be in the form of a snap ring or like element serving to dispose or maintain the valve block within the cylinder 24 against the force exerted thereon by the biasing spring 35 and in a predetermined position relative to the conduit means, as will be made more clear hereinafter.

Figure 2:
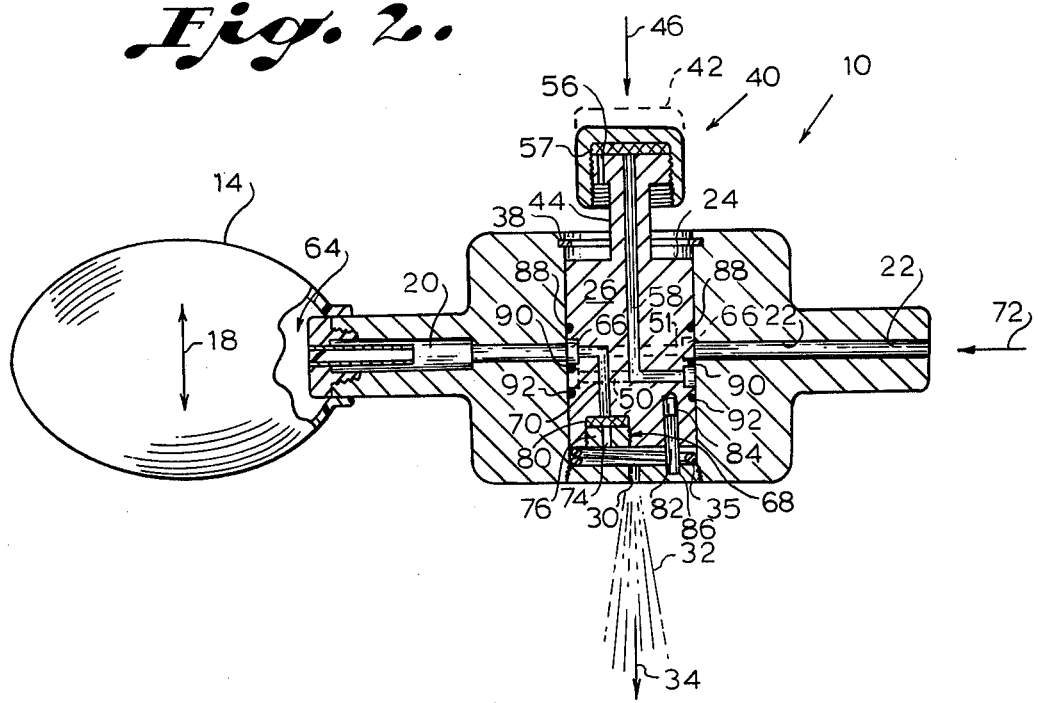
FIG. 2 is a sectional view of the embodiment of FIG. 1 showing the valve block disposed within the cylinder of the housing so as to establish direct fluid communication from the point of use back through the valve housing to the fluid exit assembly.

The valve block means further includes a position adjusting element in the form of a push knob generally indicated as 40 and including a head portion 42 rotatably and threadedly connected to the outwardly extending finger 44 which may be integrally or otherwise attached to the remainder of the valve block 26 as shown in both FIGS. 1 and 2.

Accordingly, the position of the valve block means 26 within the cylinder 24 may be determined by the downward force exerted on the push knob 40 as indicated by directional arrow 46 whereby the valve block means 26 is moved against the biasing force exerted thereon by spring element 35.

An important structural feature of the present invention comprises the provision of fluid flow path means integrally formed or otherwise disposed on the valve block means 26 as shown. More specifically, the fluid flow path means comprises a first path of fluid flow 50 disposed to establish direct fluid communication between the first conduit element 20 and the second conduit element 22. The actual path of the first fluid flow path is generally represented in broken lines in FIGS. 1 and 2 as 51 and may be formed either directly through the interior of the valve block means 26 or about the outer peripheral surface in a substantially curvilinear configuration. The position of the valve block means 26 as shown in FIG. 1 serves to allow direct fluid flow between the fluid supply source 14, first conduit element 20, valve block means 26 via first fluid flow path 50, second conduit element 22 and then to the point of use of the pressurized fluid as to a pressure cuff and sphygmomanometer head used for the taking of blood pressure as set forth above.

In addition, a relief valve means is generally indicated as 54 and comprises a relief port 56 disposed in fluid communication with a first fluid channel 58 which itself is disposed in direct fluid communication with the first fluid flow path 50 as clearly shown in both FIGS. 1 and 2. A sealing means 57 is disposed between end 59 of the first fluid channel 58 and the relief port 56 as shown. The rotational adjustment of the head 42 serves to dispose the sealing means 57 into or out of sealing engagement between port 56 and the end 59 or the first fluid channel 58. Accordingly, in the position of the valve block means 26 shown in FIG. 1 air may be released or vented directly to atmosphere upon its return from the point of use of the pressurized fluid. This occurs by the returned fluid, under pressure, as indicated by directional arrow 60, passing through the second conduit element 22, into the first fluid flow path 50 and from there to the first fluid channel 58, to the relief port 56 while the sealing means 58 is maintained out of sealing engagement with the sealing port 56. Return of pressurized fluid to the squeeze bulb or fluid supply means 14 is prevented through the provision of a one-way check valve as generally indicated by 64. This one-way check valve may be of substantially conventional design and is structured to allow fluid to flow from the fluid supply source 14, through the first conduit element 20, into the valve housing 12. However, fluid flow in the reverse direction against the check valve 64 is prevented.

The second fluid flow path 66, shown in its operative position in FIG. 2, is disposed in direct fluid communication with the first and second fluid conduit elements 20 and 22, respectively, by the depression of the push knob 40 against the biasing force exerted on the valve body by the biasing spring 34. In this position, the second fluid flow path allows returning, pressurized fluid to be vented through a fluid exit assembly generally indicated as 68 which communicates with the second fluid flow path through the second fluid channel 70. The second fluid flow path 66 is substantially, correspondingly configured to the first fluid flow path and may be integrally formed in the valve block means either around its periphery or through its interior so as to establish fluid communication as desired and set forth above. In any event, upon the depression of the valve block means 26 in the position indicated in FIG. 2 the return of the pressurized fluid as indicated by directional arrow 72 exits the valve housing 12 and more particularly the valve block 26 through metered orifice 74 having a predetermined configuration. An orifice block 76 is threaded or otherwise attached therein as shown to accomplish ready replacement thereof if so desired. The purpose of the metered orifice is to cause a venting of the pressurized fluid as indicated by directional arrow 72, coming from the pressurized cuff and sphyg head, at a consistent rate. As set forth above, this allows a consistent, efficient and more effective observation and monitoring of the sphyg head during its operation. A filter or diffuser element 80 is also disposed in direct fluid communication between the second fluid channel 70 and the metered aperture 74 as shown in both FIGS. 1 and 2.

Further structural features of the present invention is the provision of a orientation means which includes a pin element 82 secured within indentation 84 and also generally secured to the closing disc as at 86. The provision of this pin in the manner indicated in both FIGS. 1 and 2, prevents the rotation of the valve block means 26 when rotation of the head 42 of the push knob 40 occurs. As set forth above, rotation of the head 42 is accomplished so as to allow disengagement of the sealing means 58 from the exit port 56.

Additional structural features of the present invention comprises the provision of sealing means 88, 90 and 92 disposed in spaced relation to one another and on opposite sides of the first and second fluid flow paths 50 and 66. More specifically, sealing means comprising the individual sealing rings 88 and 90 are disposed on opposite sides of the second fluid flow path 66 while sealing rings 90 and 92 are disposed on opposite sides of the first fluid flow path 50. The provision of these sealing rings in this manner provides for fluid segregated disposition of the first and second flow paths relative to one another and a "leaking" of the pressurized fluid or gas from the valve block 26 out of the cylinder. Each of the individual sealing rings 88, 90 and 92 may be formed in substantially annular grooves formed on the outer periphery of the valve block 26 so as to be disposed in sealing engagement with the inner peripheral surface of the cylinder 24 as clearly represented.

It will thus be seen that the objects set forth above, among those made apparent from the preceding description, are efficiently attained, and since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A valve assembly of the type primarily designed for control of fluid flow to and from a point of use, said valve assembly comprising: a housing including fluid conduit means disposed in fluid communicating relation between said housing and a fluid source and a point of fluid use; cylinder means formed in said housing and disposed in fluid communication with said conduit means; valve block means movably disposed within said cylinder means; fluid flow path means comprising a first and second path of fluid flow disposed in spaced apart relation to one another formed in said valve block means and disposable in interconnecting relation with said conduit means; and a fluid exit assembly formed at least in part on said valve block means and disposed in fluid communication between the exterior of said valve assembly and said second path of fluid flow, said valve block means being movable into and out of fluid communicating position between said conduit means and both said first and second paths of fluid flow and said fluid exit assembly, said fluid exit assembly further comprising aperture means having a predetermined dimension, whereby flow of fluid from said valve assembly is metered dependent upon the predetermined dimension of said aperture means.

2. A valve assembly as in claim 1 further comprising relief valve means formed in said valve block and disposable in fluid communication with said fluid conduit means.

3. A valve assembly as in claim 2 wherein said relief valve means comprises a relief port, and seal means disposed in fluid sealing engagement with said relief port between said relief port and said fluid conduit means.

4. A valve assembly as in claim 3 further comprising a push knob rotationally connected to said valve block and disposable for positioning said sealing means into and out of sealing engagement with said relief port, whereby rotation of said push knob relative to said valve block serves to dispose said sealing means into and out of sealing relation to said relief port.

5. A valve assembly as in claim 1 wherein said fluid conduit means comprises a first conduit disposed between a fluid source and said valve block and a second conduit disposed in fluid communication between a point of fluid use and said valve block.

6. A valve assembly as in claim 1 further comprising check valve means disposed in fluid regulating position in said fluid conduit means between the source of fluid and said cylinder, whereby fluid is allowed to flow in one direction only from the exterior of said housing to said valve block.

7. A valve assembly as in claim 2 wherein said first path of fluid flow is disposable in fluid communication between said relief valve means and said fluid conduit means, and wherein said second path of fluid flow is disposable in fluid communication between said fluid exit assembly and said fluid conduit means, said valve block means being movable selectively to establish fluid communication between said fluid conduit means and either of said first and second paths of fluid flow, whereby fluid may selectively exit said valve assembly through said relief valve means and said fluid exit assembly.

8. A valve assembly as in claim 7 wherein each of said first and second path of fluid flow comprise a substantially curvilinear path extending at least in part about the outer peripheral surface of said valve block, each of said curvilinear paths disposed in spaced apart relation to one another and each movable into fluid communication with said fluid conduit means, whereby said relief valve means and said fluid exit assembly are selectively disposable into fluid communication with said fluid conduit means by positioning of said first and second flow paths, respectively.

9. A valve assembly as in claim 8 wherein a first fluid channel is disposed between said first fluid flow path and said relief valve, said first fluid channel formed at least in part on the interior of said valve block and integral therewith.

10. A valve assembly as in claim 9 further comprising a second fluid channel disposed between said second fluid flow path and said fluid exit means, said second fluid channel formed at least in part on the interior of said valve block and integral therewith and further disposed out of fluid communication with said first fluid channel.

11. A valve assembly as in claim 8 further comprising a plurality of sealing elements mounted on said valve block and disposed in spaced relation to one another and in sealing engagement between the outer surface of said valve block and the inner wall surface of said cylinder.

12. A valve assembly as in claim 11 wherein two of said plurality of sealing elements are disposed in spaced relation to one another and on opposite sides of each of said first and second fluid flow paths, one other of said plurality of sealing elements disposed on said valve body in sealing engagement between said first and second fluid flow paths, said first and second fluid flow paths thereby disposed in fluid segregated relation to one another.

13. A valve assembly as in claim 1 wherein said fluid exit assembly comprises orifice block means disposed contiguous one end of said valve block means and including said aperture means comprising exit port means formed therein, whereby fluid issues therefrom at a predetermined rate.

14. A valve assembly as in claim 13 wherein said fluid exit assembly further comprises closing disc means disposed contiguous one end of said cylinder means in spaced apart relation to said orifice block means and bias means disposed between said closing disc means and said one end of said valve block means, said valve block means being biased toward the other end of said cylinder means and in fluid communication between one of said first and second paths of fluid flow and said conduit means.

* * * * *